US009888867B2

(12) United States Patent
Hestness et al.

(10) Patent No.: US 9,888,867 B2
(45) Date of Patent: Feb. 13, 2018

(54) MEDICAL BREATHING APPARATUS

(71) Applicant: AIRWAY CONTROL TECHNOLOGIES, LLC, Bloomington, MN (US)

(72) Inventors: Timothy Hestness, Shakopee, MN (US); Robert Moore, Bloomington, MN (US)

(73) Assignee: AIRWAY CONTROL TECHNOLOGIES, LLC, Bloomington, MN (US)

( * ) Notice: Subject to any disclaimer, the term of this patent is extended or adjusted under 35 U.S.C. 154(b) by 688 days.

(21) Appl. No.: 14/213,719

(22) Filed: Mar. 14, 2014

(65) Prior Publication Data
US 2014/0276170 A1 Sep. 18, 2014

Related U.S. Application Data

(60) Provisional application No. 61/798,543, filed on Mar. 15, 2013.

(51) Int. Cl.
*A62B 18/02* (2006.01)
*A61B 5/097* (2006.01)
(Continued)

(52) U.S. Cl.
CPC .............. *A61B 5/097* (2013.01); *A61B 1/24* (2013.01); *A61B 5/01* (2013.01); *A61B 5/0833* (2013.01);
(Continued)

(58) Field of Classification Search
CPC ........ A61M 16/06; A61B 5/682; A61B 5/097; A61B 5/4818
See application file for complete search history.

(56) References Cited

U.S. PATENT DOCUMENTS 4,495,945 A   1/1985  Liegner
4,966,141 A * 10/1990  Bacaner .............. A61B 5/0205
                                          128/207.14
(Continued)

FOREIGN PATENT DOCUMENTS

DE   3502766 A1   7/1986
WO   9003199 A1   4/1990

OTHER PUBLICATIONS

Kodali, B.S., "Capnography Outside the Operating Rooms", Anesthesiology, vol. 118, No. 1, Jan. 2013, pp. 192-201, the American Society of Anesthesiologists, Inc. Lippincott Williams & Wilkins.

*Primary Examiner* — Patricia Mallari
*Assistant Examiner* — Karen Toth
(74) *Attorney, Agent, or Firm* — Seager, Tufte & Wickhem, LLP

(57) ABSTRACT

A medical mouthpiece may include a generally U-shaped member forming a lateral interocclusal passageway extending from an anterior aperture to a posterior aperture configured to provide a conduit for respiratory gas exchange. A medical mouthpiece may include a sampling port for fluid communication with an analyzing apparatus configured to analyze exhaled respiratory gases. A medical mouthpiece may include a supplemental gas conduit for fluid communication between a source of supplemental gas and a supply orifice. A method for delivering a gas to a patient may include delivering a gas to the patient through a mouthpiece having a lateral interocclusal passageway such that the gas is delivered through a posterior aperture to a space adjacent the patient's posterior oropharynx.

20 Claims, 9 Drawing Sheets

(51) Int. Cl.

| | | |
|---|---|---|
| A61B 17/02 | (2006.01) | |
| A61B 17/34 | (2006.01) | |
| A61B 5/083 | (2006.01) | |
| A61M 16/04 | (2006.01) | |
| A61B 5/01 | (2006.01) | |
| A61B 1/24 | (2006.01) | |
| A61B 90/30 | (2016.01) | |
| A61C 5/90 | (2017.01) | |
| A61B 5/08 | (2006.01) | |
| A61F 5/56 | (2006.01) | |
| A61M 16/08 | (2006.01) | |

(52) U.S. Cl.
CPC ........ *A61B 5/0836* (2013.01); *A61B 17/0218* (2013.01); *A61B 17/3423* (2013.01); *A61B 90/30* (2016.02); *A61C 5/90* (2017.02); *A61M 16/0493* (2014.02); *A61F 5/566* (2013.01); *A61M 16/085* (2014.02); *A61M 2202/0208* (2013.01); *A61M 2202/0283* (2013.01); *A61M 2205/7536* (2013.01); *A61M 2230/432* (2013.01); *Y02C 20/10* (2013.01)

(56) References Cited

U.S. PATENT DOCUMENTS

| | | | |
|---|---|---|---|
| 5,089,637 A | | 2/1992 | Urban |
| 5,413,095 A | | 5/1995 | Weaver |
| 5,513,634 A | | 5/1996 | Jackson |
| 5,624,257 A | * | 4/1997 | Farrell ............... A61C 7/08 128/861 |
| 5,626,128 A | | 5/1997 | Bradley et al. |
| 5,752,510 A | | 5/1998 | Goldstein |
| 5,950,624 A | | 9/1999 | Hart |
| 5,957,133 A | | 9/1999 | Hart |
| 6,209,542 B1 | | 4/2001 | Thornton |
| 6,334,064 B1 | * | 12/2001 | Fiddian-Green ... A61B 5/14539 600/311 |
| 6,379,312 B2 | | 4/2002 | O'toole |
| 6,386,199 B1 | | 5/2002 | Alfery |
| 6,422,240 B1 | | 7/2002 | Levitsky et al. |
| 6,533,582 B2 | | 3/2003 | Lindquist |
| 6,571,798 B1 | | 6/2003 | Thornton |
| 6,729,325 B2 | | 5/2004 | Alfery |
| 6,830,445 B2 | | 12/2004 | Curti |
| 6,983,744 B2 | | 1/2006 | Alfery |
| 6,997,186 B2 | | 2/2006 | Robertson et al. |
| 7,007,694 B2 | | 3/2006 | Aylsworth et al. |
| 7,118,377 B2 | | 10/2006 | Inoue et al. |
| 7,171,962 B1 | | 2/2007 | Bloem |
| 7,311,103 B2 | | 12/2007 | Jeppesen |
| 7,337,780 B2 | | 3/2008 | Curti et al. |
| 7,364,682 B2 | | 4/2008 | Curti et al. |
| 7,383,839 B2 | | 6/2008 | Porat et al. |
| 7,451,766 B2 | | 11/2008 | Miller |
| 7,624,736 B2 | | 12/2009 | Borody |
| 7,743,770 B2 | | 6/2010 | Curti et al. |
| 7,832,400 B2 | | 11/2010 | Curti et al. |
| 7,935,065 B2 | | 5/2011 | Martin et al. |
| 7,946,288 B2 | | 5/2011 | Flynn et al. |
| 8,020,276 B2 | | 9/2011 | Thornton |
| 8,091,554 B2 | | 1/2012 | Jiang |
| 8,122,889 B2 | | 2/2012 | Vaska et al. |
| 2003/0089371 A1 | | 5/2003 | Robertson et al. |
| 2005/0103347 A1 | * | 5/2005 | Curti ................. A61M 16/0666 128/207.18 |
| 2006/0112962 A1 | * | 6/2006 | Tebbutt ............. A61M 16/0488 128/206.29 |
| 2008/0216843 A1 | * | 9/2008 | Jiang ..................... A61F 5/566 128/848 |
| 2008/0308108 A1 | | 12/2008 | Diorio |
| 2010/0316973 A1 | | 12/2010 | Remmers et al. |
| 2011/0005531 A1 | | 1/2011 | Manzo |
| 2011/0180076 A1 | | 7/2011 | Hegde et al. |
| 2012/0172678 A1 | | 7/2012 | Logan et al. |
| 2012/0172679 A1 | | 7/2012 | Logan et al. |

* cited by examiner

MEDICAL BREATHING APPARATUS

REFERENCE TO RELATED APPLICATIONS

This application claims priority under 35 U.S.C. § 119(e) to U.S. Provisional Application No. 61/798,543, filed Mar. 15, 2013, the entire disclosure of which is herein incorporated by reference.

FIELD OF THE INVENTION

The present invention pertains to medical devices and methods for using medical devices. More particularly, the present invention pertains to medical devices for respiratory support.

BACKGROUND

A wide variety of devices have been developed for medical use, for example, use in the mouth or respiratory system. Some of these devices include oral appliances, oral or nasal cannulas, breathing or ventilation tubes, and the like. These devices may be used according to any one of a variety of methods. Of the known medical devices and methods, each has certain advantages and disadvantages. There is an ongoing need to provide alternative medical devices as well as alternative methods for using medical devices.

BRIEF SUMMARY

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture between the upper surface and the lower surface, the lateral interocclusal passageway configured to provide a conduit for respiratory gas exchange.

A medical mouthpiece may include a generally U-shaped member forming an upper surface configured to contact an upper dentition of a patient spaced apart from a lower surface configured to contact a lower dentition of the patient, a sampling port formed within a posterior portion of the generally U-shaped member, the sampling port having a sampling orifice recessed within the posterior portion which in some, but not all, embodiments may be facing in a posterior direction, and a sampling conduit for fluid communication between the sampling port and an analyzing apparatus configured to analyze exhaled respiratory gases.

A medical mouthpiece may include a generally U-shaped member forming an upper surface configured to contact an upper dentition of a patient spaced apart from a lower surface configured to contact a lower dentition of the patient, and a supplemental gas conduit for fluid communication between a source of supplemental gas and a supply orifice formed in the generally U-shaped member.

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture between the upper surface and the lower surface, the lateral interocclusal passageway configured to provide a conduit for respiratory gas exchange, a sampling port formed within a posterior portion of the lateral interocclusal passageway and may have a sampling orifice that may be facing in a posterior direction, the sampling port configured to be positioned in a posterior portion of a lateral interocclusal space of the patient, a sampling conduit for fluid communication between the sampling port and an analyzing apparatus configured to analyze exhaled respiratory gases, and a supplemental gas conduit for fluid communication between a source of supplemental gas and a supply orifice within the lateral interocclusal passageway.

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture along an axis defined by a line between the upper dentition and the lower dentition, the lateral interocclusal passageway configured to provide a conduit for respiratory gas exchange, a sampling port formed within a posterior portion of the lateral interocclusal passageway and may have a sampling orifice that may be facing in a posterior direction, a sampling conduit fluidly connecting the sampling port and an analyzing apparatus configured to analyze exhaled respiratory gases collected adjacent the oropharynx of the patient, and a supplemental gas conduit fluidly connecting a source of supplemental gas and a supply orifice within the lateral interocclusal passageway.

A medical mouthpiece may include a generally U-shaped first member forming an upper channel spaced apart from a lower channel with left and right lateral interocclusal passageways formed therebetween, the left and right lateral interocclusal passageways extending from an anterior portion of the first member through a posterior portion of the first member, and a first central orifice extending through the anterior portion, wherein the first member is shaped and configured to receive an upper dentition of a patient in the upper channel or a lower dentition of a patient in the lower channel, and a second member attached to the anterior portion, the second member including a second central orifice extending through the second member and in communication with the first central orifice to form a central passageway extending through the mouthpiece, wherein the second member includes a first port and a second port formed therein, the first port being fluidly connected to a left lateral interocclusal sampling port and a right lateral interocclusal sampling port for sampling expiration gases, the left and right lateral interocclusal sampling ports being disposed within the left and right inter-occlusal passageways, respectively, proximate the posterior portion, the second port being fluidly connected to the left and right lateral interocclusal passageways for delivery of a supplemental gas into the left and right lateral interocclusal passageways.

A method for delivering a gas to a patient may include inserting a mouthpiece into a mouth of a patient, the mouthpiece having a generally U-shaped member forming a lateral interocclusal passageway extending posteriorly between an upper dentition and a lower dentition of the patient, and delivering a gas to the patient through the lateral interocclusal passageway such that the gas is delivered through a posterior aperture to a space adjacent the patient's posterior oropharynx.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
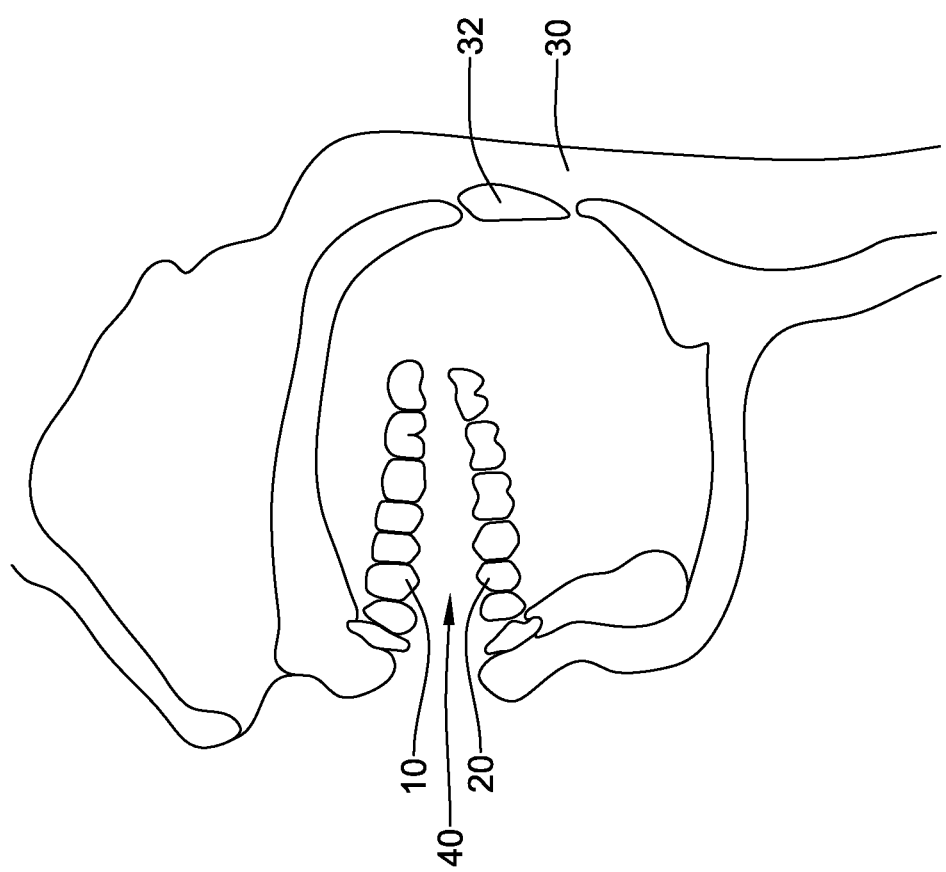
FIG. 1 is a partial side view of mouth anatomy.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

The "oral cavity" may be defined as the cavity of the mouth, particularly the part of the mouth behind the gums and teeth that is bounded above by the hard and soft palates and below by the tongue and by the mucous membrane connecting it with the inner part of the mandible.

A "dentition" refers to a character of a set of teeth, particularly with respect to number, kind, and/or arrangement. For example, the teeth of the upper jaw or maxilla may be referred to as the "upper dentition" and the teeth of the lower jaw or mandible may be referred to as the "lower dentition".

The term "interocclusal" refers to the space situated between the occlusal surfaces of opposing teeth in the two dental arches. In other words, the interocclusal space may be considered to encompass the vertical (i.e., superior-inferior) space between the upper dentition or teeth and the lower dentition or teeth. The interocclusal space may be further separated into an anterior interocclusal space generally situated between the upper and lower incisors or front teeth of the two dental arches, and a lateral interocclusal space (or spaces) generally situated outside or on either side of the upper and lower incisors and/or between the upper and lower molars of the two dental arches. In some embodiments, the lateral interocclusal space may lie generally along a line or axis following or aligned with the molars.

The "buccal cavity" may be considered to represent the area of the mouth located between the teeth and cheeks.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. While certain features may be discussed herein in the singular, it is to be understood that the details may apply to one, more than one, or all of the attendant features.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Figure 2:
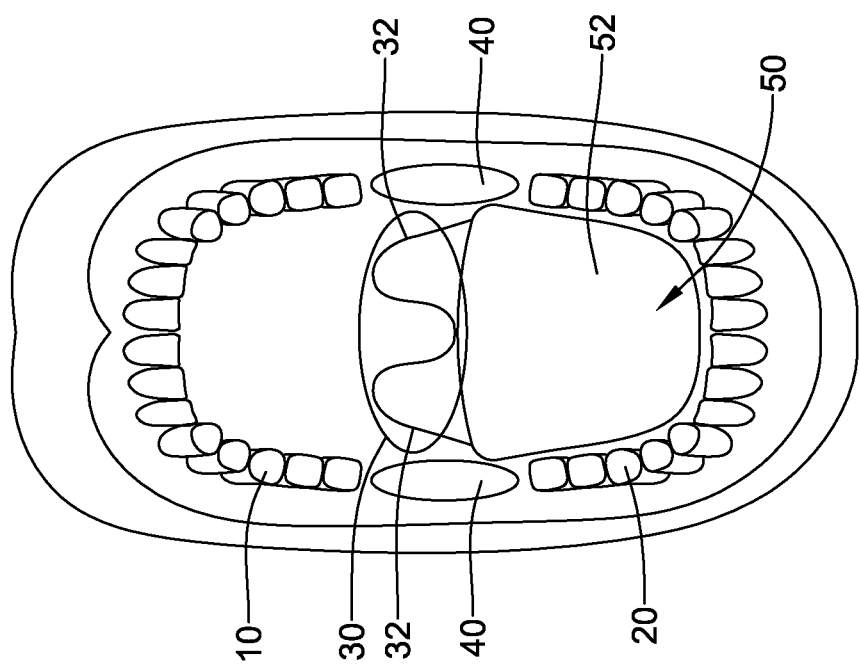
FIG. 2 is a partial front view of mouth anatomy.
Figure 3:
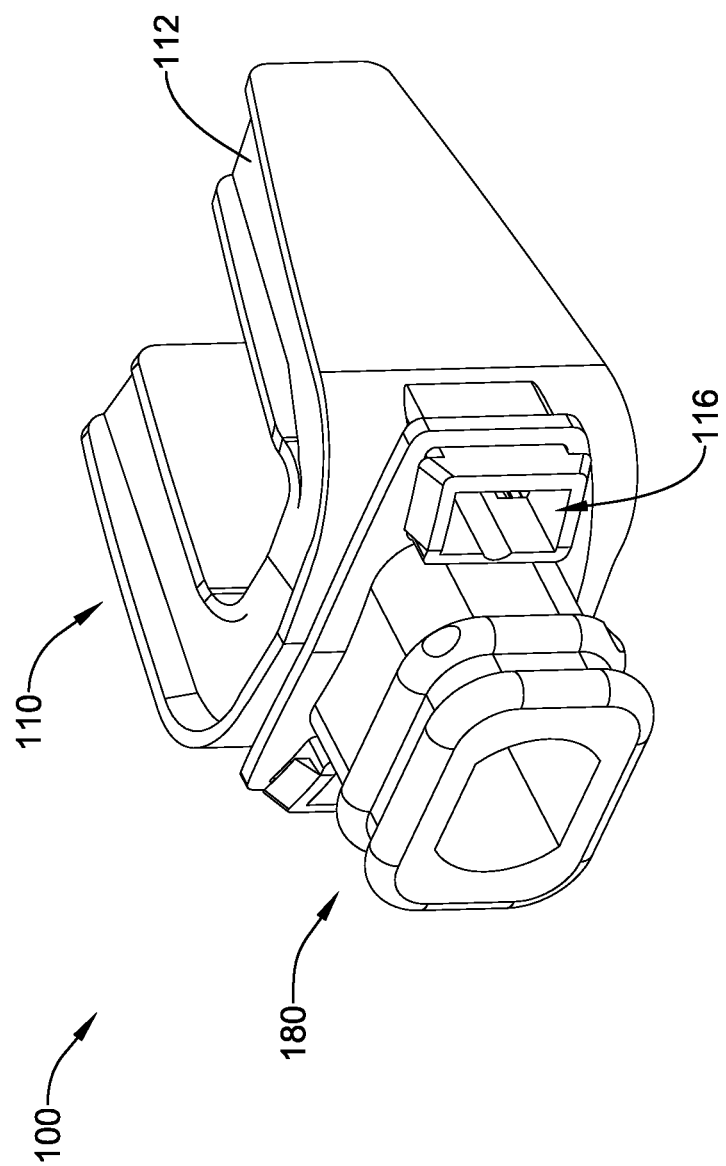
FIG. 3 is a front perspective view of an example mouthpiece.
Figure 4:
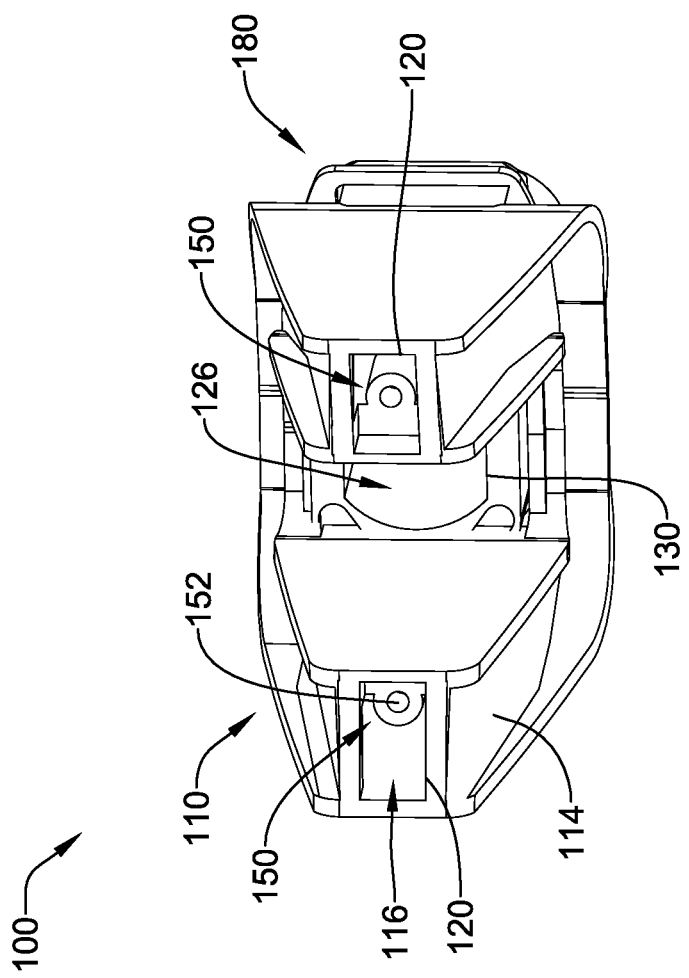
FIG. 4 is a rear perspective view of an example mouthpiece.
Figure 5:
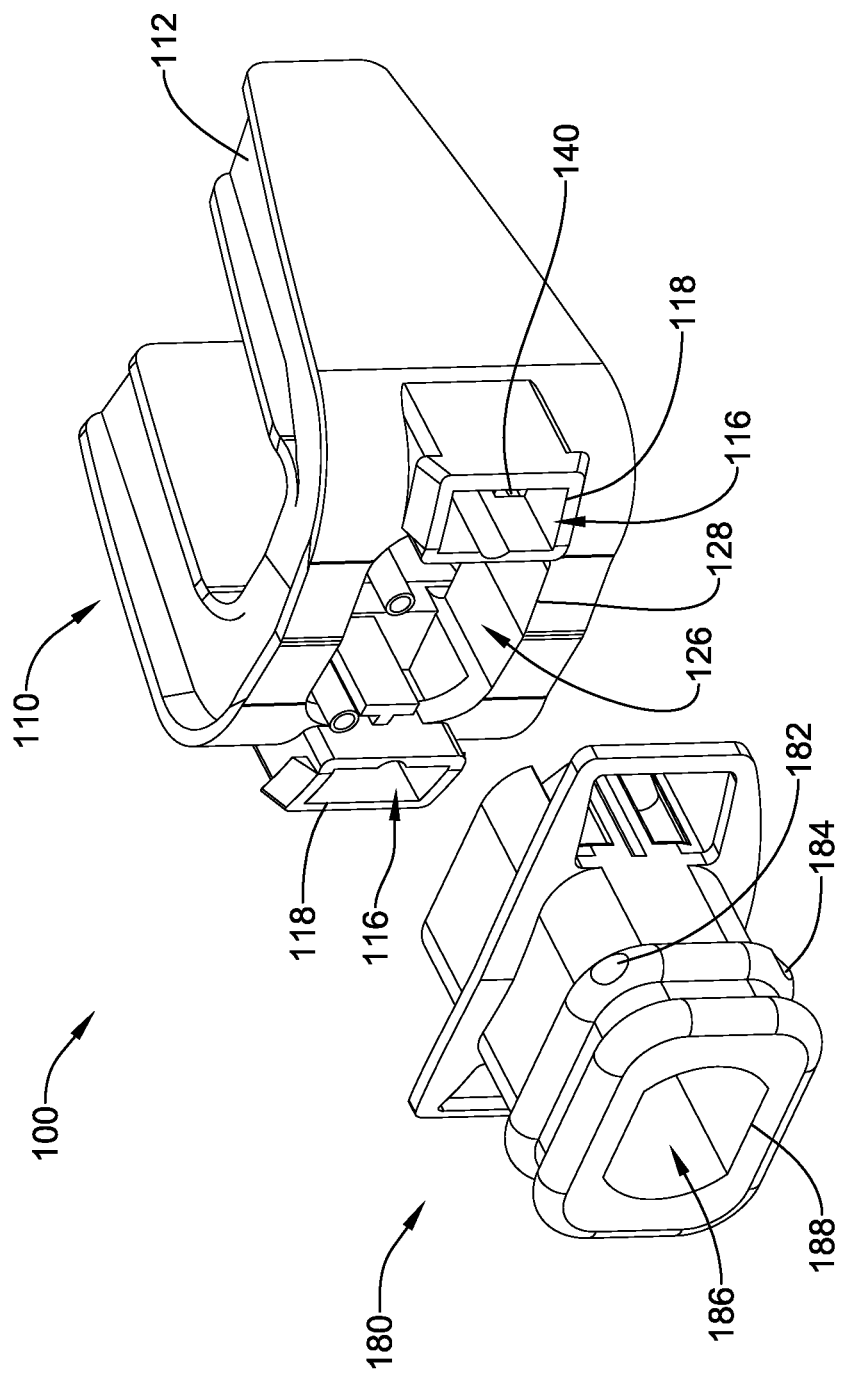
FIG. 5 is a partially exploded perspective view of an example mouthpiece.
Figure 6:
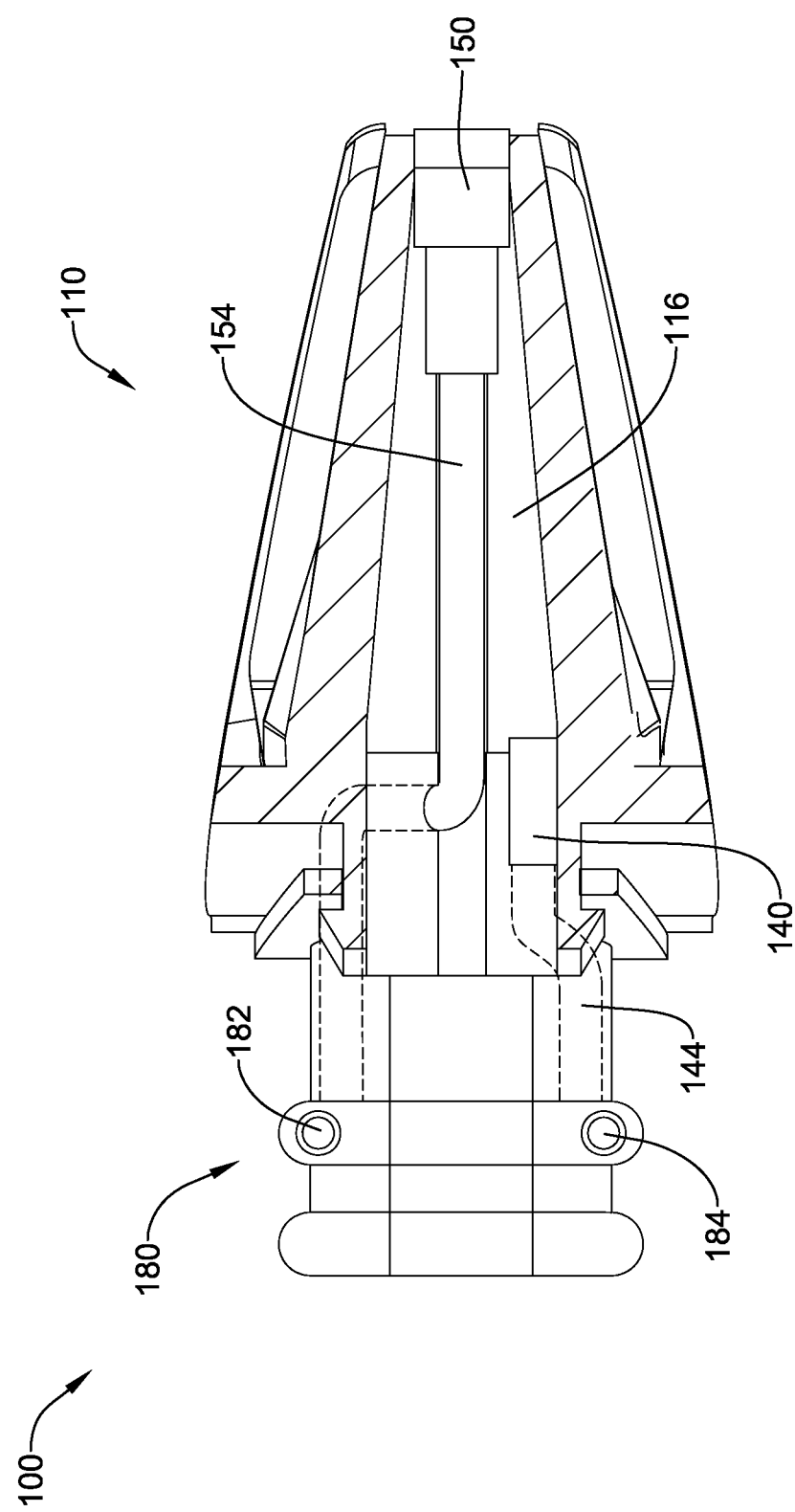
FIG. 6 is a partial cross-sectional side view of an example mouthpiece.
Figure 7:
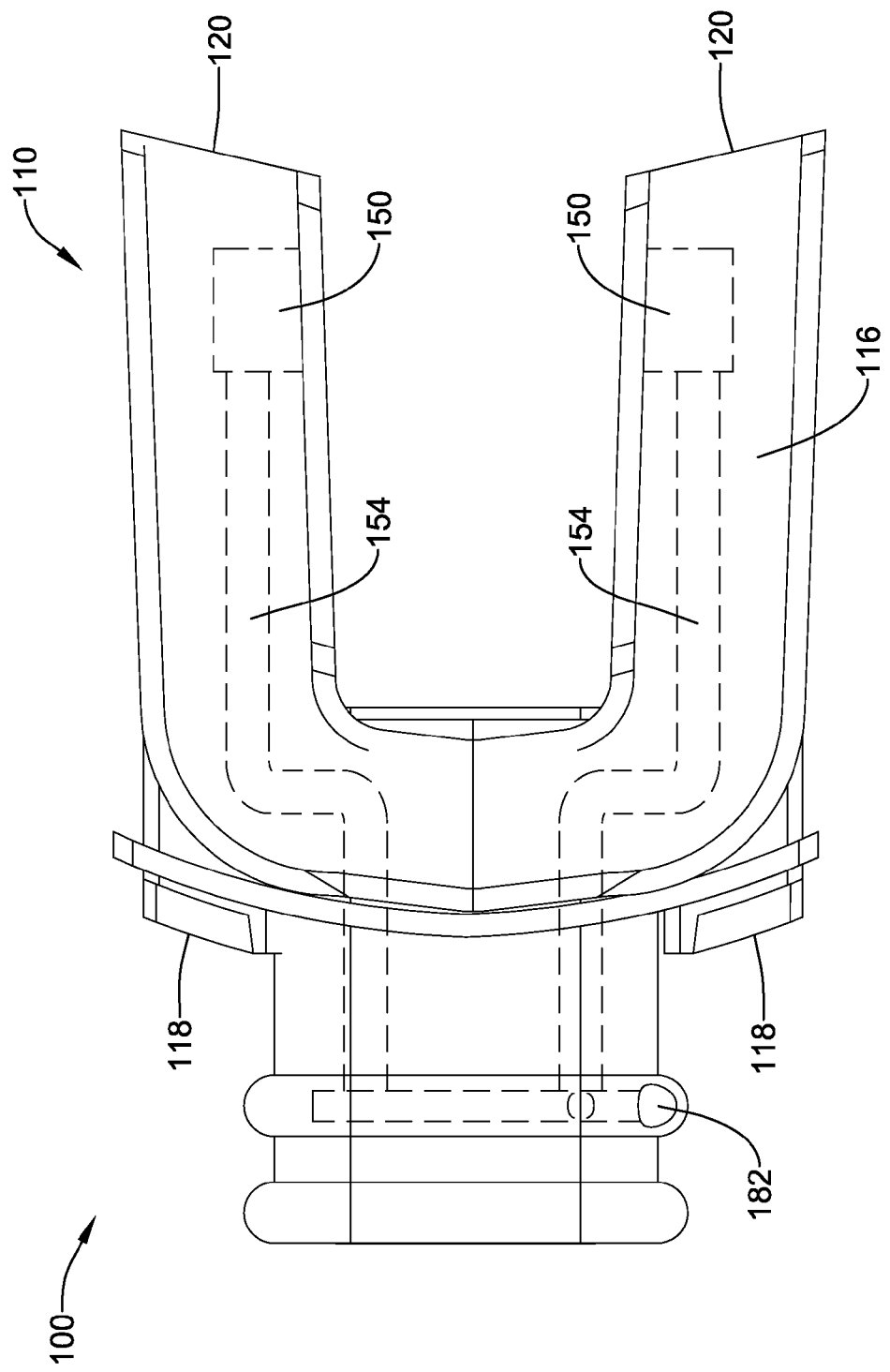
FIG. 7 is a top view of an example mouthpiece.
Figure 8:
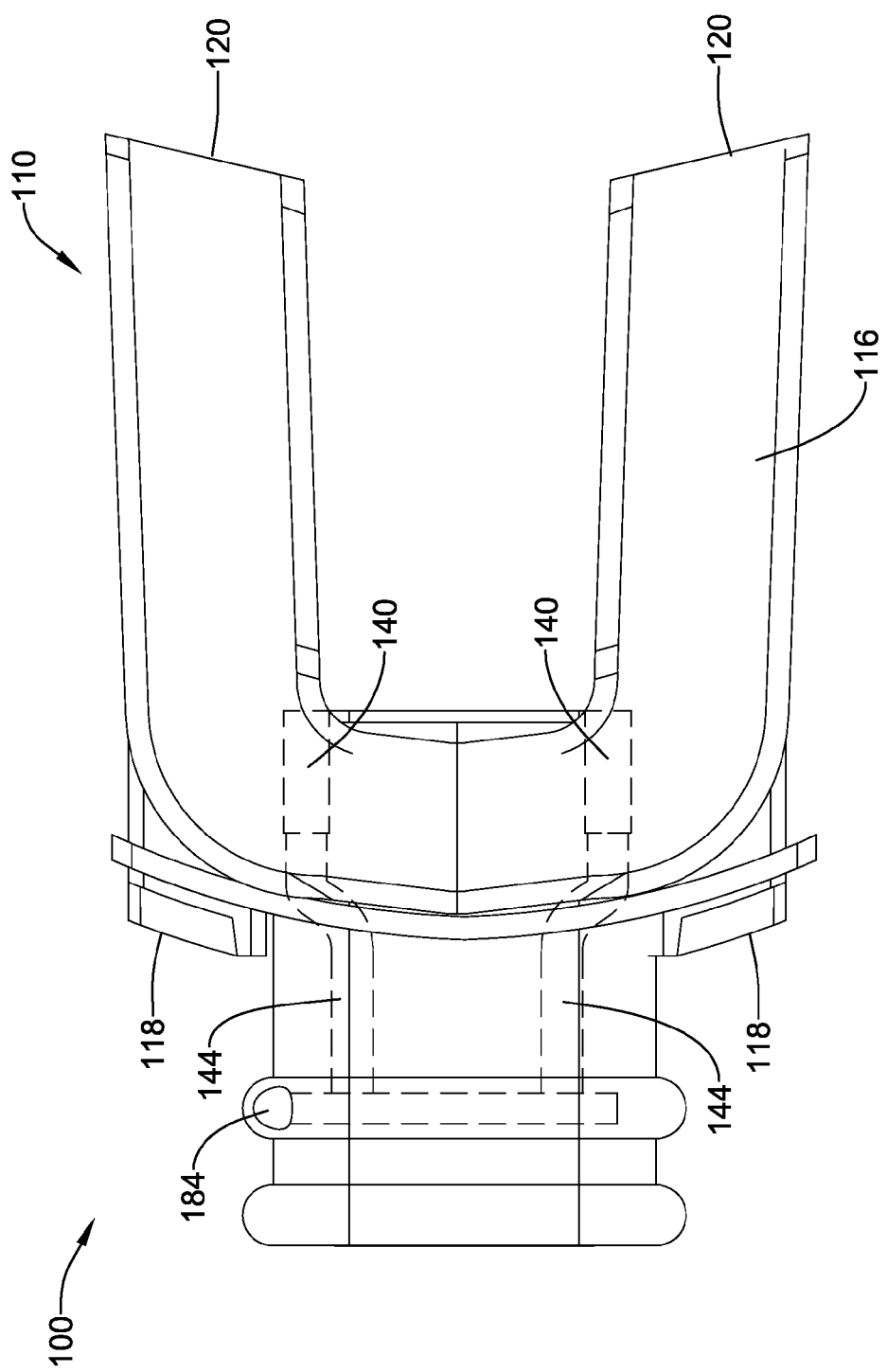
FIG. 8 is a bottom view of an example mouthpiece.

Turning now to the Figures, a partial side view of an example of portions of the anatomy of a patient's mouth may be seen in FIG. 1. The upper and lower jaws may include an upper dentition 10 and a lower dentition 20, respectively. In a normal human mouth, for example, each of the upper dentition 10 and the lower dentition 20 may include four incisors located at the front or anterior portion of the dentition and up to three molars located at a rear or posterior portion of the dentition. The third or most posterior molar may be called the wisdom tooth, and is sometimes removed for various reasons. The dentition may include two canines or cuspids, with one canine located on each side (outside or laterally) of the four incisors. Two premolars or bicuspids may be disposed between the canines and the molars along the dentition. Each dentition forms a generally U-shaped arrangement. The space between the upper dentition 10 and the lower dentition 20 may be referred to as the interocclusal space 40. More specifically, the interocclusal space located between the incisors of the upper dentition 10 and lower dentition 20 may be called the anterior interocclusal space, while the interocclusal space located laterally of the incisors and extending generally anteriorly to posteriorly between the premolars and/or the molars of the upper dentition 10 and the lower dentition 20 may be called the lateral interocclusal space. Generally speaking, the lateral interocclusal space may be bilateral and may accordingly include a left lateral interocclusal space and a right lateral interocclusal space each corresponding to an appropriate side of the patient's anatomy. Located at the rear of the mouth, and disposed on either side of the opening into the throat are the left and right anterior tonsillar pillars 32. The entrance to the throat from the mouth, and the space in the throat at the upper portion of the pharynx may generally be referred to as the oropharynx 30. The rear or posterior wall of the oropharynx is the portion of the throat which may be visibly seen at the back of the throat (behind the uvula) when viewing into a patient's mouth. FIG. 2 illustrates a frontal view of an example of portions of the anatomy of a patient's mouth. In addition to certain features described above with respect to FIG. 1, the oral cavity 50 may be seen in FIG. 2 as the central space between the molars and posterior of the incisors of the lower dentition 20. The oral cavity 50 may extend superiorly from the tongue 52 to the palate or roof of the mouth, and so occupies the central space between the molars and posterior of the incisors of the upper dentition 10, also. As seen in FIG. 2, the interocclusal space 40 includes the vertical (superior-inferior) space formed between the upper dentition 10 and the lower dentition 20 when the jaw is opened.

FIGS. 3-8 illustrate an example medical mouthpiece 100. In some embodiments, the mouthpiece 100 may be generally sized and/or shaped to fit within the anatomy of a patient's mouth. In some embodiments, the mouthpiece 100 may be a single, monolithic, or unitary structure, or may be made of multiple parts and/or components. For example the mouthpiece 100 may include a generally U-shaped first member or portion 110 and a second member or portion 180 attached to the first member 110. The first and second portions may be separate components and/or pieces, as illustrated, but in some embodiments, the first portion or member 110 and the second portion or member 180 may be integrally formed as a single member or piece. In some embodiments, the first member 110 and the second member 180 may be formed as separate pieces and later assembled together to form the mouthpiece 100. The first member 110 may be attached, connected, or otherwise coupled to the second member 180 using any appropriate means including, but not limited to, adhesive bonding, mechanical fastener(s), welding, snap fit, interference fit, friction fit, or other suitable means. In some embodiments, the first member 110 may be detachable from the second member 180.

In some embodiments, the second member 180 may include a first port 182 and a second port 184. The use, function, and structural connectivity of the first port 182 and the second port 184 will become apparent in the discussion below. In some embodiments, the second member 180 may include a central orifice 188 extending therethrough to form a portion 186 of the central passageway extending anteriorly to posteriorly through the mouthpiece 100. In some embodiments, the first member 110 may include an anterior central orifice 128 and a posterior central orifice 130. A portion 126 of the central passageway extends through the anterior portion of the first member 110 from the anterior central orifice 128 to the posterior central orifice 130. When the second member 180 is attached to the first member 110, the portion 186 of the central passageway of the second member 180 cooperates with the portion 126 of the central passageway of the first member 110 to form the complete central passageway extending through the mouthpiece 100. As will be apparent to the skilled artisan, in embodiments where the second member 180 is not present, the central passageway may be formed within the first member 110 alone. The central passageway may be configured to permit access to the oral cavity 50 when the mouthpiece 100 is positioned in the mouth of the patient. With the mouthpiece 100 positioned in the mouth of the patient, the central orifice 188 and/or the anterior central orifice 128 may be positioned exterior to the mouth of the patient, as seen for example in FIG. 9. As such, a medical instrument such as a suction device, an endoscope, an endotracheal tube, etc., for example, may be introduced into the oral cavity 50 through the central passageway as needed or desired.

In some embodiments, the first member or portion 110 may be generally U-shaped and may form or include an upper surface configured to contact the upper dentition 10 of a patient and/or a lower surface configured to contact the lower dentition 20 of a patient. In some embodiments, the upper surface may be spaced apart from the lower surface. In some embodiments, the upper surface forms an upper channel 112 configured to receive the upper dentition 10. In some embodiments, the lower surface forms a lower channel 114 configured to receive the lower dentition 20. An anterior portion of the first member 110 may include a portion of the upper and lower surfaces or channels 112/114 extending transversely (left and/or right from the medial line) between the lateral interocclusal passageways 116 (described in more detail below) to form or act as a bite block configured to be positioned between the incisors of the upper dentition 10 and the lower dentition 20. In some embodiments, the central passageway may terminate at the posterior central orifice 130 proximate a posterior portion of the upper and lower channels 112/114 extending transversely between the left and right lateral interocclusal passageways 116. In some embodiments, the upper surface (or an inferior surface of the upper channel 112) and the lower surface (or a superior surface of the lower channel 114) may angle toward each other in a posterior direction. In other words, the upper surface and the lower surface may be closer together at a posterior portion of the first member 110 than at an anterior portion of the first member 110.

In some embodiments, the first member 110 forms a lateral interocclusal passageway 116 extending from an anterior aperture 118 to a posterior aperture 120. In some embodiments, the upper surface and the lower surface may be spaced apart by the lateral interocclusal passageway 116. In some embodiments, the first member 110 may form two (i.e., left and right) lateral interocclusal passageways 116 configured to be positioned within the lateral interocclusal space(s) 40 and/or disposed on opposing sides of the oral cavity 50. In some embodiments, the lateral interocclusal passageway(s) 116 may be configured to provide a conduit for respiratory gas exchange (i.e., breathing). In at least some such embodiments, the cross-sectional area (i.e., size and/or shape) of the lateral interocclusal passageway(s) 116 may be generally sufficient to allow adequate ventilation to the patient. For example, the interocclusal passageway(s) 116, either each individually and/or collectively, may be dimensioned to have a minimum cross sectional open pathway area in the range of about 15 to about 170 mm$^2$, for example in the range of about 50 to about 150 mm², for example in the range of about 80 to about 140 mm². These ranges are believed to provide an adequate fluid pathway or conduit for respiratory gas exchange exclusively through the lateral interocclusal passageway(s) 116 within the device for most patients, but other sizes and/or ranges are contemplated for specific applications, for example, individual patient needs.

Figure 9:
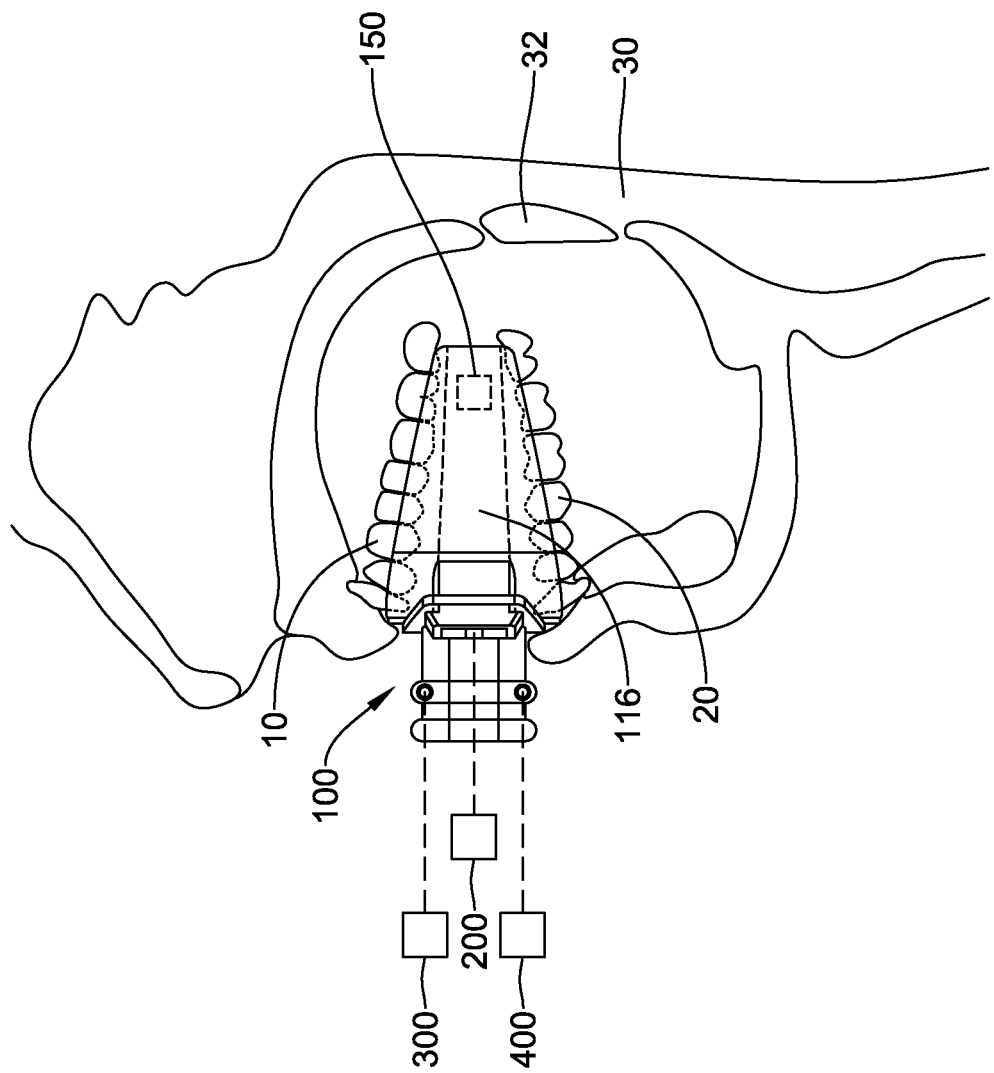
FIG. 9 is a partial side view of an example mouthpiece disposed within mouth anatomy.

In some embodiments, the anterior aperture 118 and/or the lateral interocclusal passageway(s) 116 may be fluidly and/or operatively connected to a ventilator or pressure device 200, for example as seen in FIG. 9, configured to deliver continuous or intermittent positive pressure to the posterior aperture 120, thereby delivering a respiratory gas (e.g., air) to a space adjacent the oropharynx 30 for inspiration by the patient. In some embodiments, when the mouthpiece 100 is positioned in the mouth of the patient, the anterior aperture 118 may be positioned exterior to the mouth of the patient. In some embodiments, the anterior aperture 118 may be configured to connect to known or existing airway connectors and/or devices, such as ventilator equipment, CPAP machines, nebulizers, and the like. In some embodiments having left and right lateral interocclusal passageways 116, the left and right lateral interocclusal passageways 116 may be configured or formed to combine into a single passageway for connection to an external airway connector or device. Similarly, an adapter is contemplated that may connect to both anterior apertures 118 of the left and right lateral interocclusal passageways 116 that may combine or reduce the passageways to a single external conduit with a single external opening or connector.

In some embodiments, the posterior aperture 120 is configured to avoid delivering a gas directly onto the tongue 52 of the patient. In some embodiments, the posterior aperture 120 is configured to avoid delivering a gas directly onto a cheek or directly into the buccal cavity of the patient. In some embodiments, the posterior aperture 120 is configured to deliver a gas through the lateral interocclusal space 40 of the patient. In some embodiments, the posterior aperture 120 is configured to deliver a gas to the posterior oropharynx 30 of the patient without eliciting a gag reflex. In some embodiments, the posterior aperture 120 is configured to deliver a gas to the posterior oropharynx 30 of the patient without stimulating salivation.

In some embodiments, the first member 110 may include a sampling port 150 formed within a posterior portion of the lateral interocclusal passageway(s) 116. In embodiments having more than one lateral interocclusal passageway 116, each lateral interocclusal passageway 116 may include a sampling port 150 and orifice 152 (i.e., a left lateral interocclusal sampling port and a right lateral interocclusal sampling port) formed therein. The sampling port 150 may include a sampling orifice 152 facing in a posterior direction toward the posterior aperture 120. In other embodiments, the port 150 may be facing in other directions, such as angled or facing laterally, medially, superiorly, inferiorly, or the like, or any combination thereof or angle desired. In some embodiments, the sampling port 150 and orifice 152 may be recessed from the posterior aperture 120 within the lateral interocclusal passageway 116. In some embodiments, the sampling port 150 may be generally flush with or otherwise positioned at or within the posterior aperture 120. In some embodiments, the sampling port 150 and/or the sampling orifice 152 may include a covering or valve disposed thereon. The covering or valve may be gas permeable to permit exhaled respiratory gases to pass therethrough, while being liquid impermeable to prevent liquids such as saliva or other oral secretions from entering the sampling port 150 and/or the sampling orifice 152. In some embodiments, the first member 110 may be configured to position the posterior aperture 120 and/or the sampling port 150 between a posterior edge of the second molar and the anterior tonsillar pillar 32, as may be seen in FIG. 9 for example.

In some embodiments, the sampling port 150 may be in fluid communication with and/or fluidly connected to a first port 182 and/or an analyzing apparatus 300 by a sampling conduit 154. In other words, the analyzing apparatus 300 may be operatively connected to the first port 182 and/or the sampling port 150, as seen for example in FIG. 9. In some embodiments, the sampling conduit 154 may include a discrete tubular member embedded or molded within the first member 110, a passageway or lumen integrally formed or molded within the first member 110, and/or a combination thereof. In some embodiments, the sampling conduit 154 may extend externally of the mouthpiece 100, either as an integral element or as a separate tubing or conduit element fluidly connected to the first port 182, to the analyzing apparatus 300. The analyzing apparatus 300 may be any suitable apparatus known in the art for analyzing and/or monitoring exhaled respiratory gases for, but not limited to, end tidal carbon dioxide (ETCO2) concentration, for example. In some embodiments, the analyzing apparatus 300 may compare, plot, chart, or otherwise record data such as, for example, end tidal carbon dioxide (ETCO2) concentration as a function of time.

In some embodiments, the first port 182 may be formed in the second member 180. While not expressly shown, in some embodiments, the first port 182 may be formed in the first member 110. In some embodiments, there may be no first port 182, and the sampling conduit 154 may extend directly from the sampling port 150 to the analyzing apparatus 300. In some embodiments, the first port 182 may act or function as a connector between a portion of the sampling conduit 154 disposed internal to the mouthpiece 100 and a separate, external portion of the sampling conduit 154, for example a section of tubular hose connecting the analyzing apparatus 300 to the first port 182.

In some embodiments, the first member 110 may include a supply orifice 140 formed within the lateral interocclusal passageway 116 and a supplemental gas conduit 144 in fluid communication with and/or fluidly connected to a second port 184 and/or a source of supplemental gas 400, for example, oxygen, nitrous oxide, an aerosolized pharmaceutical, or other suitable gas. In other words, the source of supplemental gas 400 may be operatively connected to the second port 184 and/or the supply orifice 140, as seen for example in FIG. 9. In embodiments having more than one lateral interocclusal passageway 116, each lateral interocclusal passageway 116 may include a supply orifice 140 (i.e., a left lateral interocclusal supply orifice and a right lateral interocclusal supply orifice) formed therein. In some embodiments, the supply orifice 140 may be configured to deliver a supplemental gas into the lateral interocclusal passageway 116. As the supplemental gas is delivered to the supply orifice 140, the supplemental gas mixes with the air or gas being delivered through the lateral interocclusal passageway(s) 116 to a space adjacent the patient's oropharynx. In some embodiments, the supplemental gas may be delivered at a flow rate of about 0.1 liters per minute to about 15 liters per minute.

In some embodiments, the first member 110 may include both a supply orifice 140 and a sampling port 150, along with any additional structure associated with each (i.e., the supplemental gas conduit 144, the sampling conduit 154, etc.). In these embodiments, the supply orifice 140 is disposed or located anteriorly of the sampling port 150. Using this arrangement or configuration, supplemental gas can be delivered to the lateral interocclusal passageway for inspiration by the patient without diluting exhaled respiratory gases being collected at the sampling port 150. As the patient exhales, exhaled respiratory gases are expelled through the lateral interocclusal passageway 116 in a posterior to anterior direction, and any supplemental gas flowing through the supply orifice 140 is expelled away from the sampling port with the exhaled respiratory gases. As such, exhaled respiratory gases may be collected at the sampling port 150 which are not diluted by the supplemental gas.

A method for delivering a gas to a patient may include inserting a mouthpiece into a mouth of a patient, the mouthpiece having a generally U-shaped member forming a lateral interocclusal passageway extending posteriorly between an upper dentition and a lower dentition of the patient. After inserting the mouthpiece, the method may include delivering a gas to the patient through the lateral interocclusal passageway such that the gas is delivered through a posterior aperture to a space adjacent the patient's posterior oropharynx. In some embodiments, the mouthpiece may include a supplemental gas conduit in fluid communication with the lateral interocclusal passageway, and the method may further include delivering a supplemental gas through the supplemental gas conduit and into the lateral interocclusal passageway, the supplemental gas mixing with the gas and being delivered to the patient's posterior oropharynx. In some embodiments, the may include a sampling port disposed within a posterior portion of the lateral interocclusal passageway, and a sampling conduit fluidly connecting the sampling port to an analyzing apparatus, and the method may further include collecting a sample of exhaled respiratory gases at the sampling port, and analyzing the sample for end tidal carbon dioxide (ETCO2) concentration. In some embodiments, the method may further include plotting the end tidal carbon dioxide (ETCO2) concentration as a function of time.

The structure and/or methods described above, and in particular the lack of structure disposed within the oral cavity, may reduce or eliminate intra-oral bulk commonly found in prior oral appliances that may displace the tongue posteriorly within the oral cavity which may contribute to or increase airway obstruction. Accordingly, the mouthpiece described herein, alone or when combined with positive airway pressure delivered through the lateral interocclusal passageway(s) to the oropharynx, may relieve or improve airway obstruction by displacing the tongue anteriorly, or permitting the tongue to move anteriorly due to lack of bulk preventing such movement, which may increase the glossopharyngeal space and/or open the oropharynx. Such improvement(s) may be beneficial for use with patients either under or recovering from anesthesia or sedation, as well as sleeping patients, such as when treating sleep apnea, for example. In some embodiments, a mandibular advancement device may be incorporated into the mouthpiece 100.

By utilizing the lateral interocclusal space, supplemental gas can be delivered posteriorly, closer to the oropharynx without the adverse effects of intra-oral devices or structures such as eliciting a gag reflex, stimulation of salivation, and/or displacing the tongue posteriorly. For example, delivering oxygen near the oropharynx may increase the opportunity for entraining supplemental oxygen independent of whether oral or nasal breathing is taking place. Delivery of oxygen and/or positive pressure near the oropharynx may increase pressure in the glossopharyngeal space, which may promote anterior displacement of the tongue and reduce airway obstruction.

Sampling of exhaled respiratory gases may be useful in several situations, such as when using capnography to monitor end tidal carbon dioxide (ETCO2) concentrations. In patients that do not have an endotracheal tube in place, such as awake or sedated patients, it may be difficult to obtain an undiluted sample of carbon dioxide due to a variety of sampling problems. For example, supplemental gases delivered at or near the sampling site may dilute the carbon dioxide sample. In another example, with some known devices or systems, exhaled respiratory gases are sampled at the mouth opening (anteriorly relative to the oropharynx) and/or nasally. Sampling at one location (i.e., at the mouth) while the patient is breathing through the other (i.e., the nose), may be problematic and/or introduce inaccuracies. It may be difficult to sample from both without a dilutional effect. Using the mouthpiece 100 described above, exhaled respiratory gases may be sampled near the oropharynx, which may reduce sampling inaccuracies from dead space dilution and entrainment of room air. Sampling near the oropharynx may also increase the chance of respiratory gas sampling independent of whether mouth breathing or nasal breathing is occurring. Additionally, the arrangement of the supplemental gas supply orifice anteriorly of the sampling port allows an exhaling patient to deliver an undiluted sample to the sampling port because exhaled respiratory gas moves anteriorly through the lateral interocclusal passageway and forces supplemental gas within the lateral interocclusal passageway(s) to be expelled anteriorly away from the sampling port during expiration, thereby increasing the accuracy of the sample by preventing dilution of the exhaled respiratory gas at the sampling port.

In at least some embodiments, portions or all of the mouthpiece 100 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the mouthpiece 100 in determining its location. Some examples of radiopaque materials can include, but are not limited to, gold, platinum, palladium, tantalum, tungsten alloy, polymer material loaded with a radiopaque filler, and the like. Additionally, radiopaque bands or markers may also be incorporated into the design of the mouthpiece 100 to achieve the same result.

In some embodiments, a degree of Magnetic Resonance Imaging (MRI) compatibility is imparted into the mouthpiece 100. For example, the mouthpiece 100, or portions thereof, may be made of a material that does not substantially distort the image and create substantial artifacts (i.e., gaps in the image). Certain ferromagnetic materials, for example, may not be suitable because they may create artifacts in an MRI image. The mouthpiece 100, or portions thereof, may also be made from a material that the MRI machine can image successfully. Some metallic materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The mouthpiece 100 may be made from or otherwise include a biocompatible polymer or polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL®available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP. In some embodiments, the anterior portion or bite block portion of the mouthpiece 100 may be formed of a stiffer or more rigid material than the posterior portion forming the lateral interocclusal passageways 116. Various combinations of hard, soft, rigid, or flexible materials may be used as desired.

In some embodiments, an exterior surface of the mouthpiece 100 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the mouthpiece 100. In some embodiments, the interocclusal passageway may include a lubricious, hydrophilic, protective, or other similar coating disposed on an inner surface thereof. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof.

In some embodiments, certain features of the present disclosure may be defined, described, or characterized according to one or more of the following aspects:

1. A medical mouthpiece, comprising:
a generally U-shaped member forming an upper surface configured to contact an upper dentition of a patient spaced apart from a lower surface configured to contact a lower dentition of the patient;
wherein the U-shaped member forms a lateral interocclusal space extending from an anterior aperture to a posterior aperture between the upper surface and the lower surface.

2. The medical mouthpiece of aspect 1, further comprising:
a sampling port formed within a posterior portion of the lateral interocclusal space the sampling port configured to be positioned in a posterior portion of the lateral interocclusal space of the patient; and
a sampling conduit for fluid communication between the sampling port and an analyzing apparatus configured to analyze exhaled respiratory gases.

3. The medical mouthpiece of aspect 1 or 2, further comprising:
a supplemental gas conduit for fluid communication between a source of supplemental gas and a supply orifice within the lateral interocclusal space.

4. A medical mouthpiece, comprising:
a generally U-shaped member forming an upper surface configured to contact an upper dentition of a patient spaced apart from a lower surface configured to contact a lower dentition of the patient;
a sampling port formed within a posterior portion of the generally U-shaped member, the sampling port having a sampling orifice recessed within the posterior portion; and
a sampling conduit for fluid communication between the sampling port and an analyzing apparatus configured to analyze exhaled respiratory gases.

5. The medical mouthpiece of aspect 4, wherein the sampling port is configured to be positioned in a posterior portion of a lateral interocclusal space of the patient.

6. A medical mouthpiece, comprising:
a generally U-shaped member forming an upper surface configured to contact an upper dentition of a patient spaced apart from a lower surface configured to contact a lower dentition of the patient; and
a supplemental gas conduit for fluid communication between a source of supplemental gas and a supply orifice formed in the generally U-shaped member.

7. The medical mouthpiece of aspect 6, wherein the supply orifice is configured to be positioned in an anterior portion of the lateral interocclusal space of the patient.

8. A medical mouthpiece, comprising:
a generally U-shaped member forming an upper surface configured to contact an upper dentition of a patient spaced apart from a lower surface configured to contact a lower dentition of the patient;
wherein the U-shaped member forms a lateral interocclusal passageway extending from an anterior aperture to a posterior aperture between the upper surface and the lower surface, the lateral interocclusal passageway configured to provide a conduit for respiratory gas exchange;
a sampling port formed within a posterior portion of the lateral interocclusal passageway, the sampling port configured to be positioned in a posterior lateral interocclusal space of the patient;
a sampling conduit for fluid communication between the sampling port and an analyzing apparatus configured to analyze exhaled respiratory gases; and
a supplemental gas conduit for fluid communication between a source of supplemental gas and a supply orifice within the lateral interocclusal passageway.

9. The medical mouthpiece of any of aspects 1-8, wherein the U-shaped member forms a central passageway extending from a central anterior orifice to a central posterior orifice;
wherein when the medical mouthpiece is positioned in a mouth of the patient, the central passageway permits access to an oral cavity of the patient for the introduction of a medical instrument therein.

10. The medical mouthpiece of any of aspects 1-3 or 8, wherein the U-shaped member forms two lateral interocclusal passageways therein, the two lateral interocclusal passageways configured to be disposed on opposing sides of an oral cavity of the patient.

11. The medical mouthpiece of aspect 8, wherein the supply orifice is disposed anteriorly of the sampling port.

12. The medical mouthpiece of any of aspects 1-3, 8, or 10 wherein the U-shaped member is configured to position the posterior aperture of the lateral interocclusal passageway between a posterior edge of a second molar and an anterior tonsillar pillar of the patient.

13. The medical mouthpiece of aspect 12, wherein the posterior aperture of the interocclusal passageway is configured to avoid delivering a gas directly onto a tongue of the patient.

14. The medical mouthpiece of aspect 12, wherein the posterior aperture of the inter-occlusal passageway is configured to avoid delivering a gas directly onto a cheek of the patient.

15. The medical mouthpiece of aspect 12, wherein the posterior aperture is configured to deliver a gas to an oropharynx of the patient without eliciting a gag reflex.

16. The medical mouthpiece of aspect 12, wherein the posterior aperture is configured to deliver a gas to an oropharynx of the patient without stimulating salivation.

17. The medical mouthpiece of any of aspects 1-3, 8, 10, or 12 wherein when the medical mouthpiece is positioned in a mouth of the patient, the anterior aperture is positioned exterior to the mouth of the patient.

18. The medical mouthpiece of any of aspects 1-3, 8, 10, 12, or 17 wherein the anterior aperture is configured to connect to respiratory equipment.

19. The medical mouthpiece of any of aspects 1-18, wherein the upper surface forms an upper channel configured to receive the upper dentition of the patient.

20. The medical mouthpiece of any of aspects 1-19, wherein the lower surface forms a lower channel configured to receive the lower dentition of the patient.

21. A medical mouthpiece, comprising:
a generally U-shaped member forming an upper surface configured to contact an upper dentition of a patient spaced apart from a lower surface configured to contact a lower dentition of the patient;
wherein the U-shaped member forms a lateral interocclusal passageway extending from an anterior aperture to a posterior aperture along an axis defined by a line between the upper dentition and the lower dentition, the lateral interocclusal passageway configured to provide a conduit for respiratory gas exchange;
a sampling port formed within a posterior portion of the lateral interocclusal passageway;
a sampling conduit fluidly connecting the sampling port and an analyzing apparatus configured to analyze exhaled respiratory gases collected adjacent an oropharynx of the patient; and
a supplemental gas conduit fluidly connecting a source of supplemental gas and a supply orifice within the lateral interocclusal passageway.

22. The medical mouthpiece of aspect 21, wherein the upper surface forms an upper channel configured to receive the upper dentition of the patient.

23. The medical mouthpiece of aspect 21, wherein the lower surface forms a lower channel configured to receive the lower dentition of the patient.

24. The medical mouthpiece of aspect 21, wherein the supply orifice is configured to deliver supplemental gas into the lateral interocclusal passageway for inspiration.

25. The medical mouthpiece of aspect 24, wherein the supplemental gas is delivered at a flow rate of about 0.1 liters per minute to about 15 liters per minute.

26. The medical mouthpiece of aspect 21, wherein the supply orifice is disposed anteriorly of the sampling port.

27. The medical mouthpiece of aspect 21, wherein the lateral interocclusal passageway is fluidly connected to a ventilator or pressure device configured to deliver continuous or intermittent positive pressure to the posterior aperture.

28. The medical mouthpiece of aspect 21, wherein the lateral interocclusal passageway is sized and configured to allow adequate ventilation to the patient.

29. The medical mouthpiece of aspect 21, wherein the analyzing apparatus is configured to monitor end tidal carbon dioxide (ETCO2) concentration in the exhaled respiratory gases.

30. A medical mouthpiece, comprising:
a generally U-shaped first member forming an upper channel spaced apart from a lower channel with left and right lateral interocclusal passageways formed therebetween, the left and right lateral interocclusal passageways extending from an anterior portion of the first member through a posterior portion of the first member, and a first central orifice extending through the anterior portion;
wherein the first member is shaped and configured to receive an upper dentition of a patient in the upper channel or a lower dentition of a patient in the lower channel; and
a second member attached to the anterior portion, the second member including a second central orifice extending through the second member and in communication with the first central orifice to form a central passageway extending through the mouthpiece;
wherein the second member includes a first port and a second port formed therein;
the first port being fluidly connected to a left lateral interocclusal sampling port and a right lateral interocclusal sampling port for sampling expiration gases, the left and right lateral interocclusal sampling ports being disposed within the left and right inter-occlusal passageways, respectively, proximate the posterior portion;
the second port being fluidly connected to the left and right lateral interocclusal passageways for delivery of a supplemental gas into the left and right lateral interocclusal passageways.

31. The medical mouthpiece of aspect 30, wherein the first port is fluidly connected to the left and right lateral interocclusal sampling ports by a left sampling conduit and a right sampling conduit, respectively.

32. The medical mouthpiece of aspect 31, wherein the first port is fluidly connected to a respiratory gas sampling apparatus configured to collect and analyze exhaled respiratory gas.

33. The medical mouthpiece of aspect 30, wherein the second port is fluidly connected to the left and right lateral interocclusal passageways by a left supplemental gas conduit and a right supplemental gas conduit, respectively.

34. The medical mouthpiece of aspect 33, wherein the second port is fluidly connected to a source of supplemental gas for inspiration.

35. The medical mouthpiece of aspect 30, wherein a posterior opening of the central passageway terminates proximate a posterior portion of the upper and lower channels extending transversely between the left and right lateral interocclusal passageways.

36. The medical mouthpiece of aspect 30, wherein an inferior surface of the upper channel and a superior surface of the lower channel angle toward each other in a posterior direction.

37. A method for delivering a gas to a patient, the method comprising:
  inserting a mouthpiece into a mouth of a patient, the mouthpiece having a generally U-shaped member forming a lateral interocclusal passageway extending posteriorly between an upper dentition and a lower dentition of the patient;
  delivering a gas to the patient through the lateral interocclusal passageway such that the gas is delivered through a posterior aperture to a space adjacent the patient's oropharynx.

38. The method of aspect 37, wherein the mouthpiece includes a supplemental gas conduit in fluid communication with the lateral interocclusal passageway, and the method further includes:
  delivering a supplemental gas through the supplemental gas conduit and into the lateral interocclusal passageway, the supplemental gas mixing with the gas and being delivered to the patient's posterior oropharynx.

39. The method of aspect 37 or 38, wherein the mouthpiece includes a sampling port disposed within a posterior portion of the lateral interocclusal passageway, and a sampling conduit fluidly connecting the sampling port to an analyzing apparatus, and the method further includes:
  collecting a sample of exhaled respiratory gases at the sampling port; and
  analyzing the sample for end tidal carbon dioxide (ETCO2) concentration.

40. The method of aspect 39, further including:
  plotting the end tidal carbon dioxide (ETCO2) concentration as a function of time.

41. The medical mouthpiece of any of aspects 2, 4, 8, or 21, wherein the sampling port includes a covering disposed thereon, the covering being impermeable to liquid and permeable to gas.

42. The medical mouthpiece of aspect 30, wherein the left and right lateral interocclusal sampling ports each include a covering disposed thereon, the covering being impermeable to liquid and permeable to gas.

43. The medical mouthpiece of any of aspects 1-5, wherein the lateral interocclusal space is configured to provide a conduit for respiratory gas exchange.

44. The medical mouthpiece of any of aspects 1-5 or 43, wherein the lateral interocclusal space is configured to provide a conduit for supplemental gas delivery.

45. The medical mouthpiece of any of aspects 1-5 or 43-44, wherein the lateral interocclusal space is configured to provide a conduit for delivery of continuous pressure.

46. The medical mouthpiece of any of aspects 1-5 or 43-45, wherein the lateral interocclusal space is configured to provide a conduit for delivery of intermittent pressure.

47. The medical mouthpiece of any of aspects 1-5 or 43-46, wherein the lateral interocclusal space is configured to provide a fluid passageway extending from the anterior aperture to the posterior aperture.

48. The medical mouthpiece of any of aspects 2, 8, or 21, wherein the sampling port has a sampling orifice.

49. The medical mouthpiece of aspect 4 or 48, wherein the sampling orifice is facing in a posterior direction.

50. The medical mouthpiece of aspect 4 or 48, wherein the sampling orifice is facing in a direction that is other than a posterior direction.

51. The medical mouthpiece of aspect 18, wherein the respiratory equipment is selected from a ventilator, an anesthesia circuit, a CPAP device, a BiPAP device, a rescue bag valve device, or combinations thereof.

52. A method for sampling exhaled respiratory gases of a patient, the method comprising:
  inserting a mouthpiece into a mouth of a patient, the mouthpiece having a generally U-shaped member forming a lateral interocclusal passageway extending posteriorly between an upper dentition and a lower dentition of the patient;
  collecting a sample of exhaled respiratory gases through at least a portion of the interocclusal passageway; and
  analyzing the sample.

53. The method of aspect 52, wherein the analyzing step includes analyzing for end tidal carbon dioxide (ETCO2) concentration.

54. The method of aspect 52 or 53, wherein the mouthpiece includes a supplemental gas conduit in fluid communication with the lateral interocclusal passageway, and the method further includes:
  delivering a supplemental gas through the supplemental gas conduit and into the lateral interocclusal passageway.

55. The method of any of aspects 52-54, wherein the mouthpiece includes a sampling port disposed within a posterior portion of the lateral interocclusal passageway, and a sampling conduit fluidly connecting the sampling port to an analyzing apparatus, and the method further includes:
  collecting a sample of exhaled respiratory gases at the sampling port.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical mouthpiece, comprising:
  a generally U-shaped member forming an upper surface configured to contact an upper dentition of a patient spaced apart from a lower surface configured to contact a lower dentition of the patient;
  wherein the U-shaped member forms a lateral interocclusal passageway extending from an anterior aperture to a posterior aperture between the upper surface and the lower surface, the lateral interocclusal passageway being configured to be positioned within a lateral interocclusal space of the patient;
  wherein the U-shaped member includes a proximal portion, a left arm member extending distally from the proximal portion, and a right arm member extending distally from the proximal portion;
  wherein the posterior aperture is disposed at a distal end of the left arm member or the right arm member.

2. The medical mouthpiece of claim 1, further comprising:
  a sampling port formed within a posterior portion of the lateral interocclusal passageway the sampling port configured to be positioned in a posterior portion of the lateral interocclusal space of the patient; and
  a sampling conduit for fluid communication between the sampling port and an analyzing apparatus configured to analyze exhaled respiratory gases.

3. The medical mouthpiece of claim 2, wherein the sampling port includes a covering disposed thereon, the covering being impermeable to liquid and permeable to gas.

4. The medical mouthpiece of claim 2, wherein the analyzing apparatus is configured to monitor end tidal carbon dioxide (ETCO2) concentration in the exhaled respiratory gases.

5. The medical mouthpiece of claim 1, further comprising:
a supplemental gas conduit for fluid communication between a source of supplemental gas and a supply orifice within the lateral interocclusal passageway;
wherein the supply orifice is configured to deliver supplemental gas into the lateral interocclusal passageway for inspiration.

6. The medical mouthpiece of claim 1, wherein the U-shaped member forms a central passageway extending from a central anterior orifice to a central posterior orifice;
wherein when the medical mouthpiece is positioned in a mouth of the patient, the central passageway permits access to an oral cavity of the patient for the introduction of a medical instrument therein.

7. The medical mouthpiece of claim 1, wherein the lateral interocclusal passageway comprises a left lateral interocclusal passageway in the left arm member and a right lateral interocclusal passageway in the right arm member, the left and right lateral interocclusal passageways configured to be disposed on opposing sides of an oral cavity of the patient.

8. The medical mouthpiece of claim 1, wherein when the medical mouthpiece is positioned in a mouth of the patient, the anterior aperture is positioned exterior to the mouth of the patient.

9. The medical mouthpiece of claim 1 wherein the generally U-shaped member is a first member, the medical mouthpiece further comprising a second member attached to the anterior portion of the first member, the anterior portion having a first central orifice extending therethrough, the second member including a second central orifice extending through the second member and in communication with the first central orifice to form a central passageway extending through the mouthpiece.

10. The medical mouthpiece of claim 1, further comprising a second posterior aperture at the distal end of the other of the right arm member or the left arm member such that both arm members comprise a single posterior aperture.

11. The medical mouthpiece of claim 10, wherein the U-shaped member further comprises a second anterior aperture in fluid communication with the second posterior aperture.

12. The medical mouthpiece of claim 1, wherein when the U-shaped member is positioned within a mouth of the patient, the posterior aperture opens away from a tongue of the patient.

13. A system comprising a ventilator or pressure device and a medical mouthpiece, the medical mouthpiece comprising:
a generally U-shaped member forming an upper surface configured to contact an upper dentition of a patient spaced apart from a lower surface configured to contact a lower dentition of the patient;
wherein the U-shaped member forms a lateral interocclusal passageway extending from an anterior aperture to a posterior aperture between the upper surface and the lower surface, the lateral interocclusal passageway being configured to be positioned within a lateral interocclusal space of the patient;
wherein the lateral interocclusal passageway is fluidly connected to the ventilator or pressure device to deliver continuous or intermittent positive pressure to the posterior aperture.

14. A medical mouthpiece, comprising:
a generally U-shaped first member forming an upper channel spaced apart from a lower channel with left and right lateral interocclusal passageways formed therebetween, the left and right lateral interocclusal passageways extending from an anterior portion of the first member through a posterior portion of the first member, and a first central orifice extending through the anterior portion;
wherein the first member is shaped and configured to receive an upper dentition of a patient in the upper channel or a lower dentition of a patient in the lower channel;
wherein the left and right lateral interocclusal passageways are configured to be positioned within left and right lateral interocclusal spaces of the patient; and
a second member attached to the anterior portion, the second member including a second central orifice extending through the second member and in communication with the first central orifice to form a central passageway extending through the mouthpiece;
wherein the second member includes a first port and a second port formed therein;
the first port being fluidly connected to a left lateral interocclusal sampling port and a right lateral interocclusal sampling port for sampling expiration gases, the left and right lateral interocclusal sampling ports being disposed within the left and right inter-occlusal passageways, respectively, proximate the posterior portion;
the second port being fluidly connected to the left and right lateral interocclusal passageways for delivery of a supplemental gas into the left and right lateral interocclusal passageways.

15. The medical mouthpiece of claim 14, wherein the first port is fluidly connected to the left and right lateral interocclusal sampling ports by a left sampling conduit and a right sampling conduit, respectively.

16. The medical mouthpiece of claim 15, wherein the first port is fluidly connected to a respiratory gas sampling apparatus configured to collect and analyze exhaled respiratory gas.

17. The medical mouthpiece of claim 14, wherein the second port is fluidly connected to the left and right lateral interocclusal passageways by a left supplemental gas conduit and a right supplemental gas conduit, respectively.

18. The medical mouthpiece of claim 17, wherein the second port is fluidly connected to a source of supplemental gas for inspiration.

19. The medical mouthpiece of claim 14, wherein a posterior opening of the central passageway terminates proximate a posterior portion of the upper and lower channels extending transversely between the left and right lateral interocclusal passageways.

20. The medical mouthpiece of claim 14, wherein an inferior surface of the upper channel and a superior surface of the lower channel angle toward each other in a posterior direction.

* * * * *